United States Patent [19]

Amer

[11] Patent Number: 5,605,902

[45] Date of Patent: Feb. 25, 1997

[54] 5-HT₂ RECEPTOR ANTAGONIST COMPOSITIONS USEFUL IN TREATING VENOUS CONDITIONS

[75] Inventor: Moh S. Amer, Santa Barbara, Calif.

[73] Assignee: Sam Amer & Co., Monecito, Calif.

[21] Appl. No.: 512,235

[22] Filed: Aug. 7, 1995

Related U.S. Application Data

[63] Continuation-in-part of PCT/US93/01485, Feb. 19, 1993, which is a continuation-in-part of Ser. No. 818,389, Jan. 9, 1992, Pat. No. 5,266,571.

[51] Int. Cl.⁶ ..................... A61K 31/495; A61K 31/445; A61K 31/44
[52] U.S. Cl. .................. 514/252; 514/254; 514/255; 514/317; 514/357
[58] Field of Search .................. 514/255, 357, 514/317, 252, 254

[56] References Cited

U.S. PATENT DOCUMENTS

| | | | |
|---|---|---|---|
| Re. 30,811 | 12/1981 | Dykstra | 424/266 |
| Re. 30,812 | 12/1981 | Dykstra | 546/193 |
| 3,931,195 | 1/1976 | Dykstra | 260/293 |
| 4,000,143 | 12/1976 | Dykstra | 260/293.67 |
| 4,064,254 | 12/1977 | Dykstra et al. | 424/267 |
| 4,202,825 | 5/1980 | Taya | 260/345.2 |
| 4,265,887 | 5/1981 | Breskman | 424/201 |
| 4,335,127 | 6/1982 | Vandenberk | 424/251 |
| 4,338,317 | 7/1982 | Temple | 424/250 |
| 4,342,870 | 8/1982 | Kennis | 544/282 |
| 4,411,901 | 10/1983 | Temple, Jr. et al. | 424/250 |
| 4,487,773 | 12/1984 | Temple, Jr. et al. | 424/250 |
| 4,539,318 | 9/1985 | Bazdwin | 514/222 |
| 4,626,433 | 12/1986 | Gros | 424/154 |
| 4,665,075 | 5/1987 | Vandenberk | 514/259 |
| 4,677,104 | 6/1987 | New | 514/222 |
| 4,985,257 | 1/1991 | Verde | 424/705 |
| 5,196,405 | 3/1993 | Packman | 514/53 |
| 5,234,914 | 8/1993 | Gallina | 514/54 |
| 5,266,571 | 11/1993 | Amer | 514/282 |
| 5,403,867 | 4/1995 | Okumura | 514/573 |

FOREIGN PATENT DOCUMENTS

| | | |
|---|---|---|
| 0037265 | 10/1981 | European Pat. Off. |
| 0184258 | 6/1986 | European Pat. Off. |
| 0274867 | 7/1988 | European Pat. Off. |
| 0526434 | 2/1993 | European Pat. Off. |
| 3247530 | 6/1983 | Germany |
| 852785 | 4/1985 | South Africa |
| 854161 | 6/1985 | South Africa |
| 9418958 | 9/1994 | WIPO |

OTHER PUBLICATIONS

Persson, et al. Journal of Hypertension 1986, 4 (Suppl. 1) 599–5101.

Persson, B. J. Pharm. Pharmacol. 1982 34:442–445.

Kalkman, H. O. et al. Journal of Pharmacology and Experimental Therapeutics, vol. 222 No. 1 1982 pp. 227–231.

Fagard, R. et al. British Heart Journal 1984 vol. 51, 149–56.

Wenting, G. J. Hypertension vol. 6. No. 1 Jan.–Feb. 1984, pp. 100–109.

Humphrey, P. P. A. J. Pharm. Pharmacol. 1982, 34:541.

Van Nueten et al. the Journal of Pharmacology and Experimental Therapeutics vol. 218 No. 1 1981, pp. 217–230.

Hedner, T. Journal of Cardiovascular Pharmacology 11(Suppl. 1): 544–548, 1988.

Van Nueten, J. Journal of Cardiovascular Pharmacology 11(Supp. 1) 5:10–515, 1988.

Cohen, M. L. et al. Hypertension vol. 5. No. 5 Sep.–Oct. 1983 pp. 676–681.

Fozard, J. R. Cardiovascular Pharmacology vol. 4, No. 5, 1982, pp. 829–838.

Hedner, T. Journal of Cardiovascular Pharmacology 7(Suppl. 7)5:148–5153 1985.

Roelens, P., 'Double–blind placebo–controlled study . . . ' Dermatogica, vol. 178, 1989, pp. 98–102.

Rooman, R. P. et al. 'Ketanserin promotes wound . . . ' Prog. Clin. Biol. Res., vol. 365, 1991, pp. 115–128.

P. A. van Zwieten, et al. "Pathophysiological and Pharmarco Therapeutic . . . " Clin. Physiol Biochem 1990–(Suppl 3:1–18).

Frazer, A. et al. "SugTypes of Receptors for Serotonin" Annu. Rev. Pharmacol. Taxicol, 1990. 307–348.

Chsuhing, D. J. "Comparison of the Serotonin . . . " Journal of Pharmacology and Experimental Therapeutics vol. 261 pp. 856 1992.

Shoji, T. et al. "Renal Vasodilatation" . . . European Journal of Pharmacology 190(1990) 247–250.

Müller–Schweinitzer, E. "Venoconstrictor Responses . . . " Cardiovascular Drugs and Therapy 1940;4:1455–1460 (1990).

Heuven–Nolsen, D. V. "5–HT1–like receptors" European Journal of Pharmacology, 191(1990) 375–382.

Blauw, G. J. "Antihypertensive Treatment . . . " Drugs 40(Suppl.4) 42–44, 1990.

Persson, B. "Antihypertensive Effects . . . Journal of Cardiovascular Pharmacology" (Suppl.1) 522–524, 1988.

Radic, Z. J. "Alterations in Serotonergic . . . " Journal of Vascular Surgery 40–47, 1991.

Sahin–Erdemli, I. "5–HT–like receptors . . . " Br. J. Pharmacol 1991, 386–390 (1990).

Alsip, N. L. "Multiple Serotonin . . . " Blood Vessels 1991; pp. 537–541.

Van Zwieten, P. A. "Pharmacological Profile . . . " Drugs 40(Suppl. 4):1–8, 1990.

Zhang, U. "Charcterization of Serotonergic . . . " Journal of Pharmacology and Experimental Therapeutics. 233–239 (1989).

(List continued on next page.)

*Primary Examiner*—Raymond Henley, III
*Attorney, Agent, or Firm*—Ladas & Parry

[57] ABSTRACT

Methods of employing compositions containing 5-hydroxytryptamine-2 (5-HT₂) receptor antagonists for the treatment of such venous conditions as varicose veins, venous insufficiency and wounds are disclosed.

15 Claims, 1 Drawing Sheet

OTHER PUBLICATIONS

Prichard, B. N. C. et al. "Serotorin :Receptors . . . " Clin Physiol Biochem, 1990 :8 (Suppl 3):120–128.

Summer, M. J. "Characterization of 5–HT . . . " Br. J. Pharmacol. (1991) 102.938–942.

DaGaire, H. "Haemodynamic Aspects . . . "Clin Physiol Biochem 1990:8(Suppl 3) 56–63.

Lai, F. M. et al. "Characterization of Serotonin . . . The Journal of Pharmacology and Experimental Therapeutics," 164–168 (1990).

Van Zwieten, P. A. et al. "The role of 5–hydroxytryptamine . . . " Br. J. Clin. Pharmac. (1990)30 695–745.

5-HT₂ RECEPTOR ANTAGONIST COMPOSITIONS USEFUL IN TREATING VENOUS CONDITIONS

This is a continuation of International Application PCT/US93/01485 filed on Feb. 19, 1993 and which designated the U.S. and which is a continuation-in-part of Ser. No. 07/818,389 filed Jan. 9, 1992, now U.S. Pat. No. 5,266,571.

This invention relates to the treatment of and to compositions containing 5-HT$_2$ receptor antagonists useful in treating such venous conditions as hemorrhoids, varicose veins, venous insufficiency and wounds. In particular it comprises use of a 5-hydroxytryptamine-2 receptor antagonist (5-HT$_2$) at an effective therapeutic dose to treat a human or animal suffering from such a condition. The 5-HT$_2$ receptor antagonist can also be administered prophylactically.

Serotonin or 5-hydroxytryptamine or 5-HT is a vasoconstrictor and a powerful stimulant of a variety of smooth muscles and nerves. A derivative of the amino acid tryptophan, 5-HT is formed predominantly in enterochromaffin or argentaffin cells of the intestinal tract. It is transported in the blood by platelets and is present in the brain and other tissues. Its pharmacological actions result in a variety of responses involving, inter alia, the cardiovascular, respiratory, and gastrointestinal systems, smooth muscles, exocrine glands, carbohydrate metabolism, sensory nerve endings, autonomic ganglia, the adrenal medulla, and the central nervous system.

Cellular reaction is determined by the type and number of receptors on the outer membrane of the cells. Consequently, one hormone can trigger different responses in different cells because it may have different receptors. Thus, the same hormone that can contract one smooth muscle cell, can also relax a skeletal muscle cell having a different receptor to the same hormone. This is true for 5-HT.

There are many receptors for 5-HT that control the various cellular responses which are mentioned above. To identify the different receptors to a specific hormone (e.g. 5-HT), several methods are used. For example, in labeling studies, the labeled hormone binds to a specific receptor. The antagonists are classified according to their ability to displace the labeled hormone from the receptor in question. Those that can displace it from a particular receptor are said to be antagonists to that receptor. Some antagonists can displace the hormone from one receptor without affecting its binding to another, and the degree of selectivity can thus be determined. In pharmacological studies, the ability of antagonists to antagonize some of the effects of the hormone thought to be related to one receptor or another are examined. A suitable example relates to the hormone histamine. Some antagonists (histamine-2 antagonists) can antagonize its acid secretory receptors with little or no effect on its lung receptors and thus inhibit acid secretion by the stomach without causing bronchodilatation. Other antagonists (histamine-1 antagonists) antagonize histamine's lung effects with almost no activity against its acid secretory effects. Biochemical studies are those in which the biochemical effects of the hormone in question can be antagonized selectively by one receptor antagonist or another.

Serotonin receptors are divided into several classes, one of which is referred to as the 5-HT$_2$ receptor. A complete discussion of such receptors will be found in "The Peripheral Actions of 5-Hydroxytryptamine" edited by John R. Fozard (Oxford University Press, 1989). Receptors for 5-HT have been classified based on the responses they produce when stimulated by 5-HT. At present four main classes and several subclasses of 5-HT receptors are generally recognized. The four main classes are:

5-HT$_1$ receptors: These receptors appear to mediate the relaxation of smooth muscles and increased heart rate.

5-HT$_2$ receptors: These receptors appear to mediate vasoconstriction and platelet aggregation.

5-HT$_3$ receptors: These receptors appear to mediate vomiting by action in the central nervous system.

5-HT$_4$ receptors: These receptors mediate effects not covered by the other three receptors.

(P. A. van Zwieten et al. "Pathophysiological and Pharmacotherapeutic Aspects of Serotonin and Serotonergic Drugs," *Clin. Physiol. Biochem.* 8 (suppl 3), 1–18, 1990 Frazer et al. "Subtypes of Receptors for Serotonin" *Ann. Rev. Pharmacol Toxicol.* 30, 307–348, 1990)).

The Frazer article shows that serotonin has different receptors sometimes mediating opposite effects. Thus a multitude of different and sometimes opposite effects can be induced by 5-HT receptor antagonists. 5-HT receptor antagonists produce different pharmacological responses depending on the type and location of the 5-HT receptor they antagonize of block. They produce a variety of different responses in the central nervous system. Peripherally, such antagonists can sometimes produce antagonistic responses. This is similar in many respects to the Histamine antagonists. Histamine-1 (H-1) antagonists inhibit bronchioconstriction but have no effect on gastric acid secretion while Histamine-2 (H-2) antagonists inhibit gastric acid secretion with no effects on the lungs. Thus a general statement that histamine antagonists should be good for acid secretion or bronchio-spasm is meaningless.

5-Hydroxytryptamine (5-HT$_2$) receptor antagonists are different from other 5-HT receptor antagonists in many respects in that 5-HT$_2$ receptor antagonists:

a. Antagonize serotonin stimulation of intra-cellular calcium levels via stimulation of phosphoinostiide hydrolysis in smooth muscle, human and rabbit platelets and astrocytes.

b. Antagonize serotonin contraction of the canine and human basilar artery while producing no hypotension.

c. Antagonize the increased vascular permeability induced by 5-hydroxytryptamine d. Antagonize the head shakes and twitches in rodents induced by serotonin.

5-HT can induce both contraction and relaxation in blood vessels. The type of responses produced depends on the type of receptor present. For example, 5-HT$_2$ receptor stimulation contracted the porcine coronary arteries (Daniel J. Cushing and Marlene L. Cohen, "Comparison of the Serotonin Receptors That Mediate Smooth Muscle Contraction in Canine and porcine Coronary Artery" *J. Pharmacol. Exptl. Therapy.* 261, 856–862, 1992) but dilated the canine renal artery (Shoji et al. "Renal vasodilation Induced by DOL, a 5-HT$_2$ Receptor Agonist, in the Canine Kidney" *Europ. J. Pharmacol.* 190, 247–250, 1990) Stimulation of 5-HT-receptors produced constriction in the canine Savenous vein (Else Muller-Schweinitzer, "Venoconstrictor Responses to Dihydroergocristine and Dihydroergotamine: Evidence for the Involvement of 5-HT$_1$ Like Receptors" *Cardiovascular Drugs and Therapy,* 4, 1455–1460, 1990), the rabbit saphenous vein, (Dicky Van Heuven-Nolsen et al. "5-HT$_1$ Like Receptors Mediate Contraction of the Rabbit Saphenous Vein" *Europ. J. Pharmacol.* 191, 375–382, 1990) but dilated the small arteriols in rat skeletal muscles (Nancy L. Alsip et al. "Multiple Serotonin Receptors on Large Arteriols in Striated Muscle" *Blood Vessels,* 28, 537–541, 1991). These are only example. For more examples see (Sahin-Erdemli et al. "5-HT$_1$ like Receptors Mediate 5-hyroxytryptamine-induced Contraction of Guinea-pig Isolated Iliac Artery" *Brit. J. Pharmacol.*, 102, 396–390, 1991; Fong M. Lai et al. "Characterization of Serotonin Receptors in Isolated Rat Intramyocardial Coronary Artery" *J. Pharmacol., Exptl. Therapy.*, 256, 164–169, 1991; Hubert Dabire et al., "Hemodynamic Aspects and Serotonin," *Clin. Physiol. Biochem.* 8 (suppl 3), 56–63, 1990; M. J. Summer, "Characterization of the 5-HT receptor Mediating Endothelium-Dependent Relaxation in Porcine Vena Cava," *Brit., J. Pharmacol.*, 102, 938–942 1991; B. N. C. Prichard and C. C. T. Smith, "Serotonin: Receptors and Antagonists-Summary of Symposium," *Clin. Physiol. Biochem.* 8 (suppl 3), 120–128, 1990, Lubo Zhang and Donald C. Dyer, "Characterization of Serotonergic Receptors Mediating Contraction of Ovine Umbilical Artery" *J. Pharmacol., Exptl. Therapy.* 255, 233–239, 1990).

In fact 5-HT can mediate both contraction and relaxation in the same tissue (Zeljko S. Radic et al., "Alterations in Serotonergic Receptor Expression in Experimental Vein Grafts;" *J. Vascular Surgery* 14, 40–47, 1991).

Tissues respond to hormones only if they possess specific receptors capable of recognizing and interacting with the hormone in question. The selective and sometimes opposite responses of different tissues to the same hormone, in this case 5-hydroxytryptamine (5-HT) or serotonin, is determined by the type and density of the receptors to the hormone that exist in the particular tissue. It is not possible to predict the activity of 5-HT receptor antagonists in a particular disease condition unless the tissue involved in that disease is tested. For example, 5-HT will not contract the colon vein of cats or dogs since the colon veins from both animals species have no 5-HT receptors. 5-HT will contract the human colon vein because the human colon vein contains 5-HT$_2$ receptors that mediate contraction. (see example below). In the human colon, 5-HT$_2$ receptor antagonists are expected to antagonize the increased contraction of the colonic veins induced by 5-HT (shown in the data) and decrease the vascular permeability that mediate the swelling and discomfort of hemorrhoids. Other 5-HT receptor antagonists (as 5-HT1 1A, 1B, 1C, 1D, 1P and 3) will not mediate these effects and are expected to have no beneficial effects in treating hemorrhoids, varicose veins, venous insufficiency and the healing of wounds.

In the past, before the inventor's present understanding of the different receptors and actions of 5-HT was discovered, it was customary to regard all 5-HT receptor antagonists as constituting one category and to assign common actions to all of them. This was what was done in South African Patent 85/2785 (Merck & Co). This reference as well as U.S. Pat. No. 4,665,075 (Vandenberk), European Patent 0037265 (Kennis), South African Patent 854161 (Merck) and U.S. Pat. No. 4,539,319 (Baldwin) suggest, without support, a connection between anti-serotonin activity and anti-hemorrhoidal effects. None of these references show any applicable data. Patents published in the 1980's generally assumed that anti-serotonin activity should translate into anti-hemorrhoidal effects mince the hemodynamic effects should, on theoretical grounds, be helpful. In addition, most anti-hypertensive drugs were thought to possess anti-hemorrhoidal activity. This has no basis in fact.

Specific 5-HT$_2$ receptor antagonists produce several effects including inhibition of platelet aggregation and decreasing vascular permeability. 5-HT$_2$ receptor antagonist compounds have traditionally been used as anti-anxiety agents, antidepressants, antipsychotics, anti-migraine agents or as modifers of certain other CNS functions. 5-HT$_2$ receptor antagonists, do not cause vasodilation in the arteries and do not lower blood pressure. This is shown in the example below where the 5-HT$_2$ receptor antagonist 2'[2-(1-methyl-2-piperidyl)ethyl]cinnamanilide hydrochloride do not lower blood pressure. This is so exemplified by ritanserine and ICI 169, 369 (Gerard J. Blauw et al., "Antihypertensive Treatment with Ketanserine Shows No Evidence of Vascular Serotonin-Receptor and alpha-Adrenoceptor Blockade" *Drugs*, 40 (suppl 4), 42–44 1990; P. A. van Zwieten et al. "The role of 5 hydroxytryptamine and 5-hydroxytraminerigic Mechanisms in Hypertension, "*Brit J. Clin. Pharmacol.*, 30, 695–745, 1990: Bengt Persson, et al., "Antihypertensive Effects of Ketanserine and Ritanserine in the Spontaneously Hypertensive Rat," *J. Cardiovasc. Pharmacol.*, 11 (suppl. 1. 522–524, 1988). The compounds disclosed in South African patent 85/2785 all lower blood pressure indicating that they could not be selective 5-HT$_2$ receptor antagonists.

Serotonin is not a general endogenous vasoconstrictor. Its effects in the different blood vessels varies depending on the location and size of the vessel in question (P. A. van Zwieten et al., "Pharmacological Profile of Antihypertensive" *Drugs* with Serotonin Receptor and alpha-Adrenoreceptor Activity Drugs 40 (suppl 4) 1–8, 1990). Hemorrhoids is a disease of veins not arteries. Drugs that are expected to have beneficial activity in hemorrhoids must be able to antagonize the contractile effects of 5-HT on the colon vein. Hemorrhoids is a varicose dilation of veins in the superior or inferior hemorrhoidal plexus, resulting from a persistent increase in venous pressure" (Dorland's Illustrated Medical Dictionary, 25th Edition, W. B. Saunders, Philadelphia, 1974).

Hemorrhoids refer to a mass of dilated veins in swollen tissue situated near the anal sphincter. They are believed to result from a persistent increase in venous pressure, which may be due, in part, to a constriction of the large downstream colonic veins. Occlusion due to platelet aggregation and thrombus formation may also contribute to the symptoms of hemorrhoids by interrupting blood flow and increasing blood stasis and tissue congestion.

Varicose veins are enlarged, twisted superficial veins. Varicose veins partially result from incompetent venous valves that may be acquired or congenital.

Venous insufficiency results from increase tone (partial constriction) of the deeper veins (particularly in muscles) which impedes good circulation and results in blood pooling and stasis. This is turn results in pain, tenderness and edema. The problem appears to be related to inadequate draining of the leg veins due to constriction of the exit vein valves. 5-hydroxytryptamine (5-HT or serotonin) is released from the blood platelets when the blood sits around for a long time and is thought to mediate the contraction of the exit veins.

In wounds, 5-HT is released from blood platelets causing venous constriction and interfering with good drainage and circulation. Good drainage and circulation are needed for proper and fast healing of the wounds.

This invention is directed to compositions or medicines useful in treating or preventing such conditions as hemorrhoids, varicose veins, venous insufficiency and wounds. In particular it comprises use of a 5-hydroxytryptamine-2 receptor antagonist (5-HT$_2$) to treat an animal or human, in need of such treatment. The 5-HT$_2$ receptor antagonist can also be used prophylactically. The 5-HT$_2$ receptor antagonist is used at an effective therapeutic dose. Preferred 5-HT$_2$ receptor antagonists include 2'[2-(1-methyl-2-piperidyl- )ethyl]cinnamanilide hydrochloride; 2-[3-[4(3-chlorophenyl)-1-piperazinyl]propyl]-5-ethyl-2,4-dihydro-4-(2-phenoxyethyl)-3H-1,2,4-triazol-3-one hydrochloride, 8-[4-[4-(1,2-benzisotriazol-3-yl)-1-piperazinyl]butyl]-8-azaspiro[4,5]decane-7,9-dione hydrochloride and any mixture thereof. The 5-HT$_2$ receptor antagonist 2'-[2-(1-methyl-2-piperidyl)-ethyl]cinnamanilide hydrochloride is disclosed and claimed in U.S. Pat. No. Re. 30, 811 (Dysktra et al. Mead Johnson & Company). The 5-HT$_2$ receptor antagonist 2-[3-[4-(3-chlorophenyl)-1-piperazinyl]propyl]-5-ethyl-2,4-dihydro-4-(2-phenoxyethyl)-3H-1,2,4-triazol-3-one hydrochloride is disclosed in U.S. Pat. Nos. 4,339,317 and 4,497,773. The 5-HT$_2$ receptor antagonist 8-[4-[4-(1,2-benzisothiazol-3-yl)-1-piperazinyl]butyl]-8-azaspiro[4,5]decane-7,9-dione hydrochloride is disclosed in German Patent DE 3,247,530 and U.S. Pat. No. 4,411,901.

Figure 1:
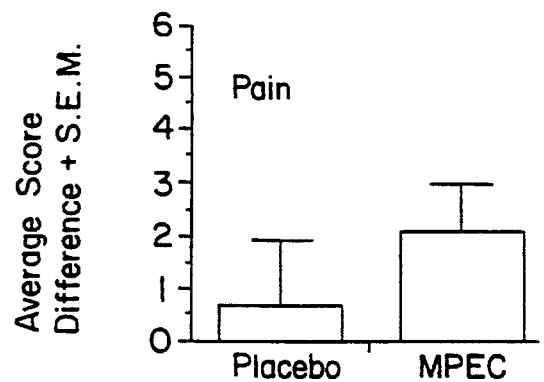
FIG. 1 illustrates the effect of 2'[2-(1-methyl-2-piperidyl)-ethyl]cinnamanilide hydrochloride (MPEC) on hemorrhoidal pain as compared to a control.

In a series of experiments using rings of human colon veins representative 5-HT$_2$ receptor antagonists were found to produce highly surprising results in blocking the contractile effects of 5-HT on the human colon. Human colonic vein rings were isolated from discarded human colon tissue following surgery (colostomy). The rings were prepared immediately after surgery and were suspended in buffered physiological saline. The contractions produced by the rings in response to the addition of 5-HT in vitro were measured. The effects of three selected 5-HT$_2$ receptor antagonist compounds on antagonizing 5-HT contractile effects were also determined.

The following tables list the three compounds used and the activity of each in blocking the contractile effects of 5-HT on the human colon in vitro. Table A also includes the activities of the three compounds on four receptors to determine receptor selectivity.

Compound I as used herein has the chemical formula: 2'[2-(1-methyl-2-piperidyl)ethyl]cinnamanilide hydrochloride, and has the following structural formula:

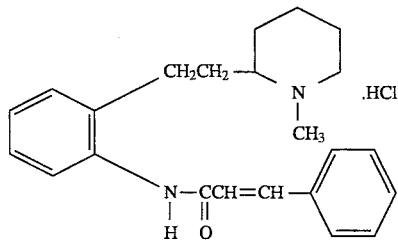

compound II as used herein has the chemical formula: 2-[3-[4-(3-chlorophenyl)-1-piperazinyl]propyl]-5-ethyl-2,4-dihydro-4-(2-phenoxyethyl)-3H-1,2,4-triazol-3-one hydrochloride, and has the following structural formula:

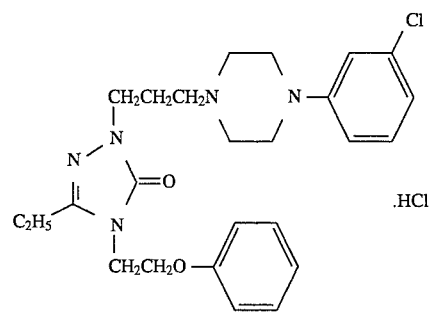

Compound III as used herein has the chemical formula: 8-[4-[4-(1,2-benzisothiazol-3-yl)-1-piperazinyl]butyl]-8-azaspiro[4,5]decane-7,9-dione hydrochloride, and has the following structural formula:

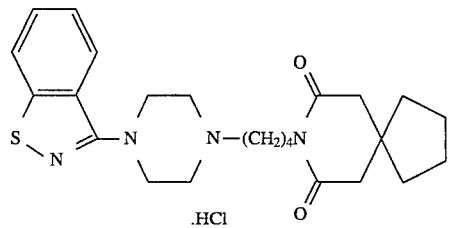

TABLE A

| Receptor Blocking Profile (IC - 50; nm) [nM = nanomolar or $1 \times 10^{-9}$M] | | | |
|---|---|---|---|
| Receptor | Compound I | Compound II | Compound III |
| 5-HT2 | 3.4 | 17.0 | 1.7 |
| 5-HT1 | 22,000.0 | >1,000.0 | 12.5 |
| Dopamine-2 | >1000.0 | >1000.0 | 8.4 |
| Alpha-receptor | >1000.0 | 160.0 | 47.0 |

The IC-50 is the concentration that inhibits agonist binding to the receptor by 50%. The better the blocker a compound is, the smaller is the concentration thereof needed to block the receptor, i.e., the smaller the IC-50, the better receptor blocker or antagonist the compound is.

The activity is determined as follows: Rings of human colon veins are prepared and hung in a tissue bath. The contractions of the rings are monitored. Adding 5-HT causes the rings to contract. Pre-addition of increasing concentrations of the antagonist result in lesser contractions. The amount of antagonist causing a 50% inhibition of the contractions is then calculated.

The receptor blocking profile is determined as follows: Labeled 5-HT is mixed with a purified preparation containing the receptor. The amount of labeled material that attaches itself to the receptor and cannot be washed off is calculated. In a series of other similar tubes, the same quantity of labeled 5-HT is mixed with increasing concentrations of the antagonist which will antagonize the binding of 5-HT to the receptor. Decreasing quantities of the labeled material will bind to the receptor. The concentration of the antagonist that inhibits the binding of 50% is then calculated.

TABLE B

Activity against 5-HT on the human colon in vitro

| IC-50 | $2 \times 10^{-9}$ (I) | $10^{-8}$ (II) | $10^{-9}$ (III) |
| --- | --- | --- | --- |

As is evident from the above data, although the compounds I, II, and III possess widely different activities against the different receptors tested, their activities in blocking the contractile effects of 5-HT on human colon rings correlated best with their 5-HT$_2$ blocking potencies.

Since these three compounds differ significantly from each other chemically, one can conclude that their antagonism of the effects of 5-HT on the human colon is due primarily to their function in blocking the 5-HT$_2$ receptors in that tissue. Thus, other 5-HT$_2$ receptor antagonists, irrespective of their chemical structure or other properties, should antagonize 5-HT and block its contractile effects on the human colon.

An experiment was performed and established that 2'[2-(1-methyl-2-piperidyl)ethyl]cinnamanilide hydrochloride (MPEC) does not lower blood pressure. This is a classical pharmacological experiment designed to test the effects of new drugs on blood pressure:

Beagle hounds of either sex weighing 8–20 kg were acclimated (18°–29° C., humidity 30–70%) for a minimum of 21 days with automatically controlled illumination (12 hours light/12 hours dark) prior to use. Each animal received approximately 300 grams of Purina Lab Canine Diet #5006 daily which was adjusted as needed for each animal to maintain appropriate body weight. Husbandry practices and veterinary care were in accordance with the Guide for Care and Use of Laboratory Animals (NIH Publication No. 85-23) Animals were fasted on the morning of the experiment and anesthetized with pentobarbital sodium 35 mg/kg i.v. Each animal was intubated with cuffed endotracheal tube to maintain respiration with Bird Mark 7 respirator. Arterial blood pressure (right femoral artery) was measured with Statham P23Db or P23Gb pressure transducer (Gould Statham Instruments, Halo Rey, PR). Heart rate was calculated from the pressure recordings. Other parameters were also monitored. The right femoral vein was cannulated for administration of supplemental anesthesia, and the left femoral vein for administration of vehicle or test drug. When give intravenously, MPEC in a dose of 1 mg/kg elicited no effect on blood pressure or heart rate. A dose of 10 mg/kg w as lethal in both dogs tested.

Figure 2:
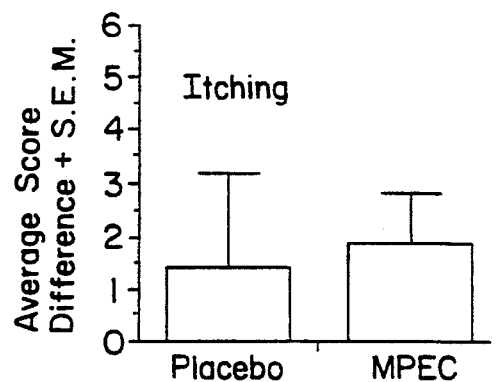
FIG. 2 illustrates the effect of MPEC on hemorrhoidal itching as compared to a control.
Figure 3:
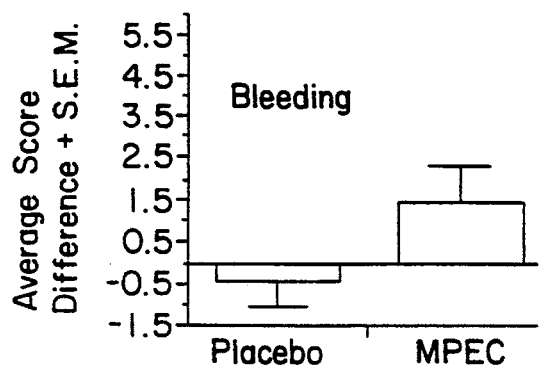
FIG. 3 illustrates the effect of MPEC on hemorrhoidal bleeding as compared to a control.
Figure 4:
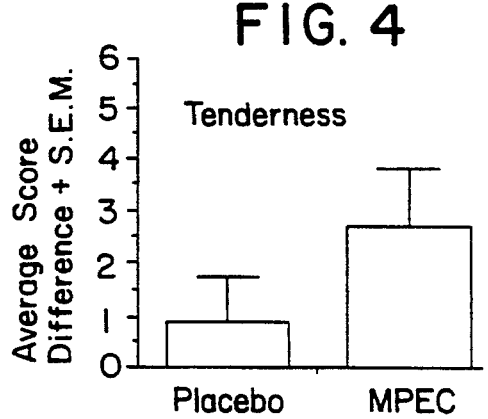
FIG. 4 illustrates the effect of MPEC on hemorrhoidal tenderness as compared to a control.
Figure 5:
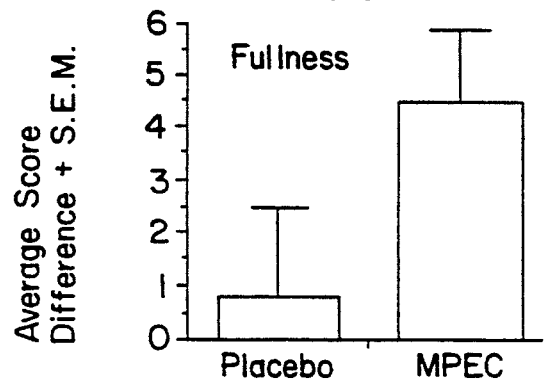
FIG. 5 illustrates the effect of MPEC on hemorrhoidal fullness as compared to a control.
Figure 6:
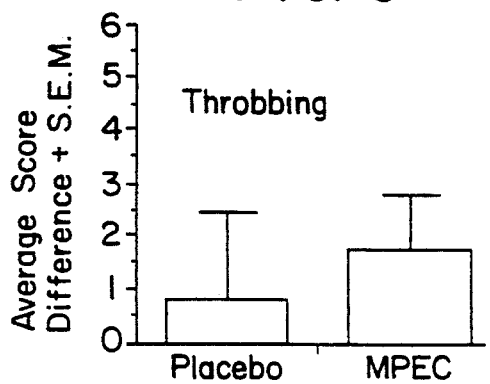
FIG. 6 illustrates the effect of MPEC on hemorrhoidal throbbing as compared to a control.

The effects of MPEC on patients with hemorrhoids was studied. This was a double-blind study. The drug was applied as a 1% cream three times a day. Patients maintained a symptom diary each day. The diary included evaluation of each symptom on a 10 point scale. The results described represent the improvements in the scale between days 1 and 5. The results are depicted in accompanying FIGURES, FIGS. 1–6. The actual numbers of score improvements were as follows:

| Parameter | Placebo | MPEC | % Improvement |
| --- | --- | --- | --- |
| Pain | 0.71 | 2.14 | 301.4 |
| Itching | 1.42 | 2.00 | 140.8 |
| Bleeding | −0.43 | 1.43 | >1000.0 |
| Tenderness | 0.86 | 2.71 | 315.1 |
| Fullness | 0.80 | 4.50 | 562.5 |
| Throbbing | 0.80 | 1.75 | 218.8 |

The results also support the conclusion that MPEC is working in hemorrhoids via 5-HT$_2$ receptor blockade since the main effect appears to be on fullness and bleeding. It is expected that a product blocking 5-HT$_2$ receptors in the colon veins will help with the drainage and will reduce the feeling of fullness that patients with hemorrhoids feel. Since there will be less blood trapped in the swollen veins, less bleeding is also expected. None of the medications presently available on the market have an effect on these two parameters.

The 5-HT$_2$ receptor antagonists of this invention may be used topically or systemically, and they may be taken orally, in liquid, powder, table or capsule form; parenterally, by intravenous, subcutaneous, or intramuscular injection; transdermally, topically by direct application in the form of a cream, gel, or ointment; rectally by suppository or enema; or by inhalation therapy. The 5-HT$_2$ receptor antagonists of this invention may be prepared and used in any suitable solid or liquid form, e.g. powder, cream, paste, table, lozenge, gel, chewing gum, solution, suspension, emulsion, salve, aerosol or the like. They may also be incorporated into wound dressings such as bandages, adhesive strips, and other forms designed to be used for wounds. These pharmacological agents may be administered in admixture with a pharmaceutically acceptable carrier or a dermatologically acceptable carrier for the topical preparations.

The compositions contain the active ingredient in an amount ranging from less than 1% to over 99%, with the remainder being a pharmaceutically acceptable or dermatologically acceptable solid or liquid carrier, which may contain other conventional excipients. Example of such carriers and excipients include fillers, binders, flavors, sweetners, bulking and coloring agents, antioxidants, anionic, nonionic, cationic, zwitterionic, and amphoteric surface active detergents, sudsing, dispersing and emulsifying agents, buffering and pH adjusting agents, water and organic solvents, humectants, thickeners, preservatives, stabilizers, mold release agents, disintegrates, anti-disintegrants, lubricants and the like. Examples of conventional pharmaceutically acceptable carriers and excipients are profusely disclosed in the prior art including discussions in U.S. Pat. No. 4,515,772 (Parran et al. Procter & Gamble), U.S. Pat. No. 4,966,777 (Gaffar et al., Colgate-Palmolive Company), and U.S. Pat. No. 4,728,512 (Mehta et al. American Home Product.), which discussion are incorporated herein by reference thereto.

The topical compositions typically contain from 0.1 to 20 weight % of a 5-HT$_2$ receptor antagonist. Preferably, they contain from 0.5 to 10 weight %. More preferably, from 1–5 weight %.

Transdermal compositions typically contain from 0.1 to 20 weight % of a 5-HT$_2$ receptor antagonists. Preferably, they contain from 0.5 to 10 weight %. More preferably, from 1–5 weight %.

Suppositories typically contain from 0.1 to 20 weight % of a 5-HT$_2$ receptor antagonist. Preferably, they contain from 0.5 to 10 weight %. More preferably, from 1–5 weight %.

Wound dressings typically contain from 0.1 to 20 weight % of a 5-HT$_2$ receptor antagonist. Preferably, they contain from 0.5 to 10 weight %. More preferably, from 1–5 weight %.

Suitably the compositions of this invention consist of sufficient material to provide a dose of from 0.05–10 mg. per kg. of body weight, more suitably 0.2–6 mg/kg body weight. These compositions may be taken 1–3 times daily or as needed until the pain or symptoms of the condition have subsided.

It will be understood that the foregoing discussion including the examples, only illustrates the invention and its principles. However, many modifications and variations in the details of the disclosure will occur to those skilled in the art to which this invention relates and still remain within the scope and principles of the invention. For example, the illustrative embodiments of the invention deal primarily with several specific 5-HT$_2$ receptor antagonists. It is apparent, however, that the principles of the invention can be applied to other 5-HT$_2$ receptor antagonists as well.

I claim:

1. A method for treating or preventing varicose veins comprising administering to an afflicted or susceptible patient a non-blood pressure-reducing 5-HT$_2$ receptor antagonist at a therapeutically effective dose.

2. A method according to claim 1, wherein the 5-HT$_2$ receptor antagonist is 2'[2-(1-methyl-2-piperidyl)ethyl]cinnamanilide hydrochloride; 2-[3-[4-(3-chlorophenyl)-1-piperazinyl]propyl]-5-ethyl-2,4-dihydro-4-(2-phenoxyethyl)-3H-1,2,4-triazol-3-onehydrochloride;8-[4-[4-(1,2-benzisothiazol-3-yl)-1-piperazinyl]butyl]-8-azaspiro[4,5] decane-7,9-dione hydrochloride; or any mixture thereof.

3. The method according to claim 2, wherein said 5-HT$_2$ receptor antagonist is administered in admixture with a pharmaceutically acceptable carrier.

4. The method of claim 1 wherein said 5-HT$_2$ receptor antagonist is administered topically or systemically.

5. The method of claim 2 wherein said 5-HT$_2$ receptor antagonist is administered topically or systemically.

6. A method for treating or preventing venous insufficiency comprising administering to an afflicted or susceptible patient a non-blood pressure-reducing 5-HT$_2$ receptor antagonist at a therapeutically effective does with the proviso that said patient is not afflicted with or susceptible to hemorrhoids.

7. A method according to claim 6, wherein the 5-HT$_2$ receptor antagonist is 2'[2-(1-methyl-2-piperidyl)ethyl]cinnamanilide hydrochloride; 2-[3-[4-(3-chlorophenyl)-1-piperazinyl]propyl]-5-ethyl-2,4-dihdyro-4-(2-phenoxyethyl)-3H-1,2,4-triazol-3-onehydrochloride;8-[4-[4-(1,2-benziothiazol-3-yl)-1-piperazinyl]butyl]-8-azaspiro[4,5] decane-7,9-dione hydrochloride; or any mixture thereof.

8. The method according to claim 7, wherein said 5-HT$_2$ receptor antagonist is administered in admixture with a pharmaceutically acceptable carrier.

9. The method of claim 6, wherein said 5-HT$_2$ receptor antagonist is administered topically or systemically.

10. The method of claim 7, wherein said 5-HT$_2$ receptor antagonist is administered topically or systemically.

11. A method for treating wounds comprising administering to an afflicted patient a non-blood pressure-reducing 5-HT$_2$ receptor antagonist at a therapeutically effective dose.

12. A method according to claim 11, wherein the 5-HT$_2$ receptor antagonist is 2'[2-(1-methyl-2-piperidyl)ethyl]cinnamanilide hydrochloride; 2-[3-[4-(3-chlorophenyl)-1-piperazinyl]propyl]-5-ethyl-2,4dihydro-4-(2-phenoxyethyl0-3H-1,2,4-triazol-3-onehydrochloride;8-[4-[4-(1,2-benziothiazol-3-yl)-1-piperazinyl]butyl]-8-azaspiro[4,5] decane-7,9-dione hydrochloride or any mixture thereof.

13. The method according to claim 12, wherein said 5-HT$_2$ receptor antagonist is administered in admixture with a pharmaceutically acceptable carrier.

14. The method of claim 11 wherein said 5-HT$_2$ receptor antagonist is administered systemically or topically.

15. The method of claim 12 wherein said 5-HT$_2$ receptor antagonist is administered systemically or topically.

* * * * *

UNITED STATES PATENT AND TRADEMARK OFFICE
CERTIFICATE OF CORRECTION

PATENT NO. : 5,605,902
DATED : February 25, 1997
INVENTOR(S) : MOH S. AMER

It is certified that error appears in the above-indentified patent and that said Letters Patent is hereby corrected as shown below:

On title page, after 63, delete "-in-part".

At column 9, line 26 (Claim 2, line 5), "onehydrochloride" should be -- one hydrochloride --.

At column 10, line 8 (Claim 7, line 4), "dihdyro" should be -- dihydro --.

At column 10, line 9, (Claim 7, line 5), "onehydrochloride" should be -- one hydrochloride --.

At column 10, line 10, (Claim 7, line 6), "benziothiazol" should be -- benzisothiazol --.

At column 10, line 25, (Claim 12, line 4), "2,4dihydro" should be -- 2,4 dihydro --.

At column 10, line 26, (Claim 12, line 5), "onehydrochloride" should be -- one hydrochloride --.

At column 10, line 27, (Claim 12, line 6), "benziothiazol" should be -- benzisothiazol --.

Signed and Sealed this

Fifteenth Day of July, 1997

Attest:

Attesting Officer

BRUCE LEHMAN

Commissioner of Patents and Trademarks